United States Patent [19]

McGee

[11] 4,135,498
[45] Jan. 23, 1979

[54] DEVICE FOR MAKING BODY MEASUREMENTS OF A PATIENT OR THE LIKE

[76] Inventor: George L. McGee, Rte. 4, Box 55, Lewisburg, W. Va. 24901

[21] Appl. No.: 787,008

[22] Filed: Apr. 13, 1977

[51] Int. Cl.$^2$ .............................................. A61B 5/10
[52] U.S. Cl. .................................. 128/2 S; 33/174 D
[58] Field of Search ............... 33/174 D, 2 R, 27 C, 33/93–94; 128/2 S; 353/23, 44, DIG. 2–4

[56] References Cited

U.S. PATENT DOCUMENTS

| | | | |
|---|---|---|---|
| 1,807,438 | 5/1931 | Ross | 33/94 |
| 1,856,779 | 5/1932 | Montelius | 33/174 |
| 2,547,425 | 4/1951 | Yonkler | 33/2 R |
| 2,780,004 | 2/1957 | Rosenbaum | 33/174 D |
| 3,753,293 | 8/1973 | Branda et al. | 33/174 D X |

FOREIGN PATENT DOCUMENTS

| | | | |
|---|---|---|---|
| 1541118 | 5/1969 | Fed. Rep. of Germany | 128/2 S |
| 947036 | 1/1964 | United Kingdom | 33/2 R |
| 830036 | 3/1960 | United Kingdom | 33/2 R |
| 163385 | 9/1964 | U.S.S.R. | 33/174 D |

Primary Examiner—Robert W. Michell
Assistant Examiner—Frank Jaworski
Attorney, Agent, or Firm—Larson, Taylor & Hinds

[57] ABSTRACT

A device for making physical measurements with respect to the body of a patient is provided which includes a non-opaque sheet-form viewing screen mounted in a frame. The screen includes centrally located, vertically extending graduations and a graduated, horizontally extending measuring bar is mounted for vertical movement relative to the vertical graduations on the screen. An angle measuring device in the form of a rotatable angle measuring arm and an associated indicator plate is mounted for movement along the measuring bar. An x-ray light box is pivoted for movement into and out of an operative position behind the screen.

7 Claims, 4 Drawing Figures

DEVICE FOR MAKING BODY MEASUREMENTS OF A PATIENT OR THE LIKE

FIELD OF THE INVENTION

The present invention relates to devices and instruments for making measurements with respect to the body of a patient, or the like, such as are utilized in checking posture, in determining the extent of injuries and in similar uses.

BACKGROUND OF THE INVENTION

Doctors and other medical personnel are often interested in obtaining data with respect to the physical measurements of the body of a patient. For example, where a serious break or dislocation of a joint has been caused by accident, disease, or the like, so as to result in a permanent or semi-permanent disfigurement of the patient, it is helpful to know reasonably precisely the degree, in physical terms, of the disfigurement. Thus, where a lateral shoulder "droop", i.e., a situation where one shoulder is lower than the other, is caused by, for example, a spinal injury, the amount of droop can be important in determining the extent of the injury and the possibility of permanent disability. In this latter regard, the extent, in measurable physical terms, of an injury may be determinative in attempting to prove disability.

One known form of a device for making measurements of the type referred to above comprises an open frame, including side and top frame members, behind which the patient stands and a plurality of resilient members, e.g., rubber bands, which are stretched across the frame around the vertically extending side frame members thereof. The device also includes measuring tapes or rules which extend along the entire height of both sides of the frame members and along the top frame member. A centrally located string or the like extending between the top and bottom of the frame serves as a center reference. In use of the device for a typical, exemplary case, a rubber band is aligned with, for example, the angle of slant of the shoulders of a patient standing behind the frame, and measurements made, using the graduated tapes on both side frame members to determine the amount of slope by comparing the points at which the rubber band intersects the tapes on the two side frames. The angle of the shoulder slant or slope can be calculated using values corresponding to the difference between the measurements on the two sides, and the width of the frame.

A somewhat similar device for measuring posture is disclosed in U.S. Pat. No. 2,111,648 (Stone). The Stone patent discloses an open frame and a plurality of indicator rods which are movable with respect to the sides of the frame and serve a function similar to that of the rubber bands referred to above. A centrally located plumb line and associated plumb bob provide a reference. It will be appreciated that the device discussed in the Stone patent as well as the device discussed above, suffer a number of disadvantages. For example, both devices are awkward to use and are limited in the kinds of measurements that can be made directly.

A number of other devices have been developed for making similar measurements in three dimensions and reference is made to U.S. Pat. Nos. 3,826,006 (Ruskin) and 3,995,285 (Moeckl) for examples of such devices. Moreover, a further patent of possible interest in U.S. Pat. No. 1,856,779 (Montelius) which discloses a highly specialized measuring instrument particularly adapted for skull measurements such as the angle of Ramus. The Montelius patent is of interest in view of the disclosure therein of a measuring box including a protractor assembly which is laterally movable along guides, and a vertically adjustable measuring square.

Although the prior art devices discussed above perform adequately within their limitations, a need exists for a device or instrument which will provide accurate physical measurements with respect to the body of a patient, including direct measurements of angular relationships as well as linear measurements, and will accomplish this in a straightforward manner with a minimum of manipulative steps and without the need for specialized training.

SUMMARY OF THE INVENTION

In accordance with the invention, a measuring device is provided which is of the general type described hereinabove and which possesses the characteristics discussed. The device of the present invention is extremely versatile and enables rapid, direct measurements of angles and angular relationships as well as other planar geometrical relations. The device of the invention is relatively inexpensive as compared with devices of the prior art providing the equivalent or more complex measurements and provides substantial advantages with respect to rapidity and flexibility in use over conventional devices of comparable cost.

According to a preferred embodiment thereof, the device of the invention comprises a frame construction behind which the patient stands whose body measurements are to be determined. The frame construction comprises a frame and a non-opaque sheet-form viewing screen which is mounted by said frame and provides viewing of at least the silhouette of a patient standing behind said screen. The viewing screen preferably includes a measuring grid provided on the surface thereof, as well as vertically extending measurement graduations centrally disposed on the viewing screen. A horizontally extending, vertically movable measuring bar, graduated in measuring units along the length thereof, is mounted on the frame for relative movement with respect to said vertically extending measuring means. In addition, an angle measuring means is mounted on measuring bar for movement along the length thereof. The angle measuring means including a pivotably mounted measuring arm and indicator means for indicating the angular position of the pivotably mounted measuring arm. Advantageously, the pivotably mounted measuring arm is also graduated in measuring units along the length thereof.

Preferably, the device of the invention also includes an x-ray light box mounted on the frame so as to be movable between an inoperative or rest position and an operative position wherein the light box is positioned behind the screen and flush therewith so as to provide illumination of x-rays affixed to the screen. With this arrangement, the measuring apparatus of the invention can also be used to make measurements relative to such x-rays.

Other features and advantages of the invention will be set forth in, or apparent from, the detailed description of a preferred embodiment found hereinbelow.

DESCRIPTION OF A PREFERRED EMBODIMENT

Figure 2:
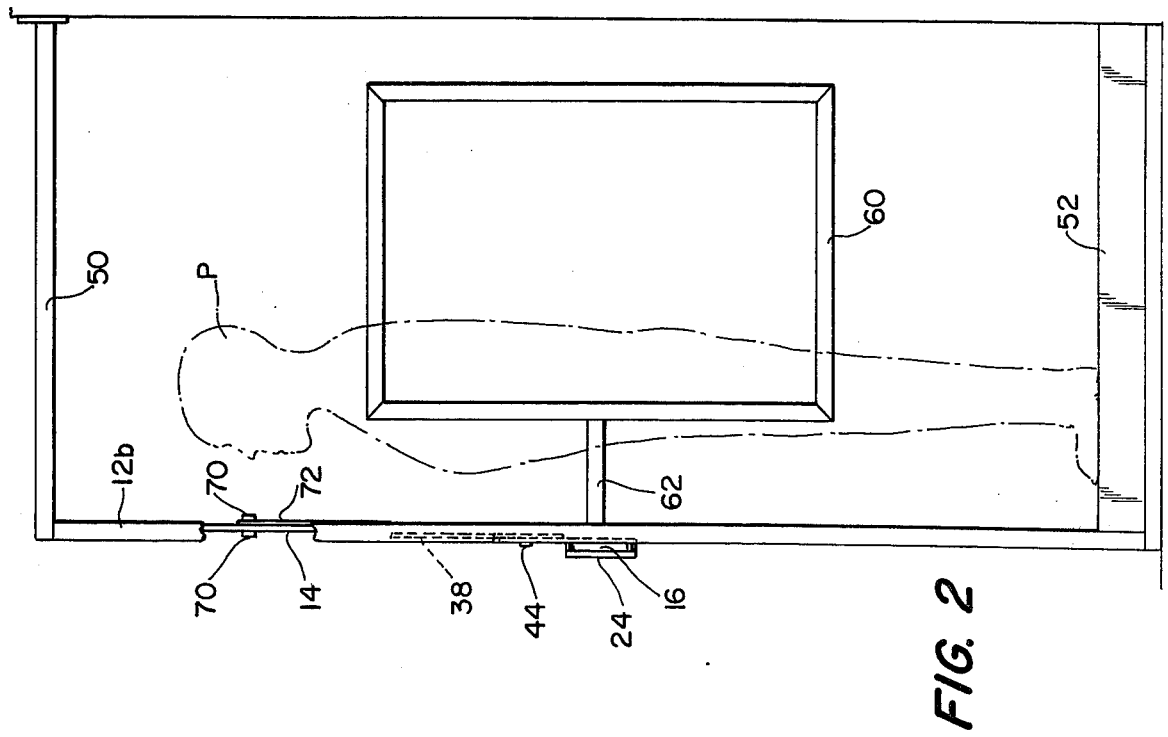
FIG. 2 is a side elevational view of the device of FIG. 1, with an associated x-ray light box shown in the inoperative position thereof.
Figure 1:
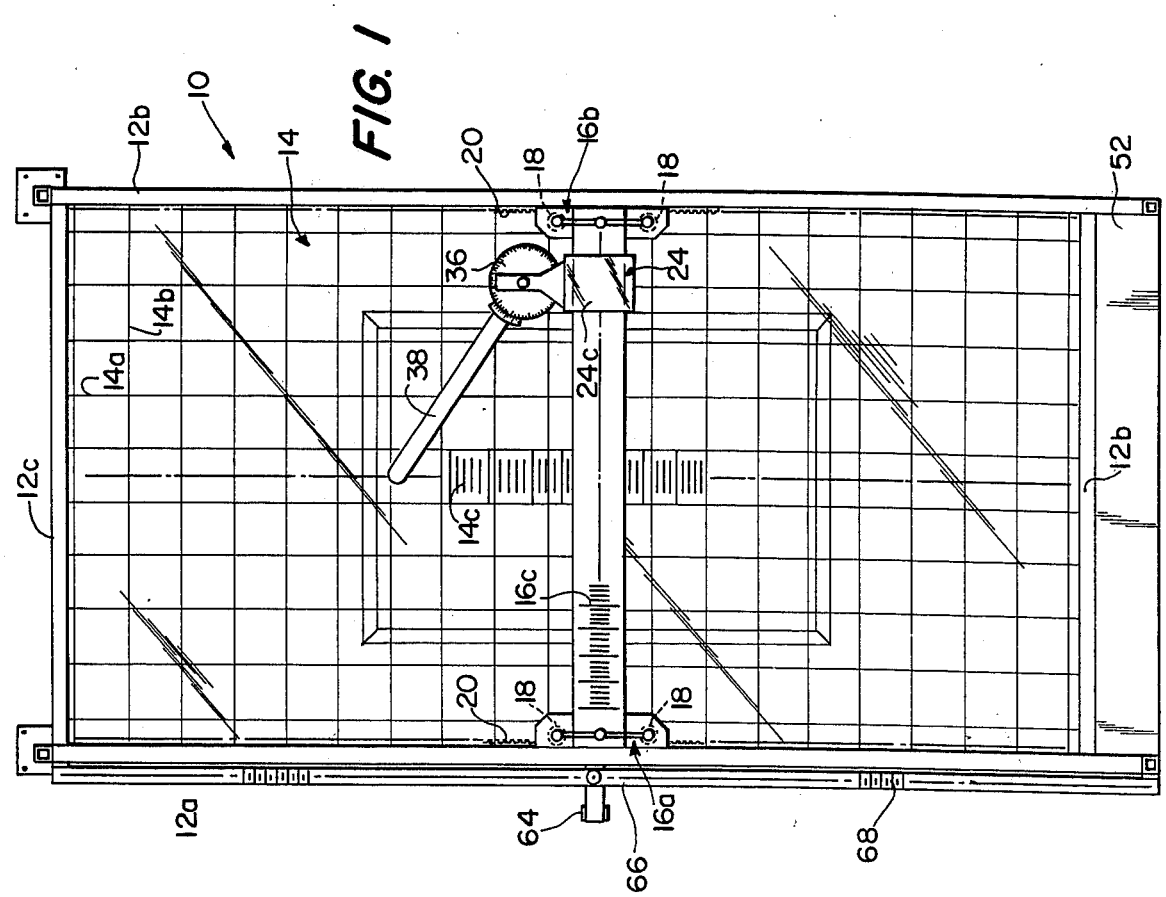
FIG. 1 is a front elevational view of a body measuring device construction in accordance with a preferred embodiment of the invention.

Referring particularly to FIGS. 1 and 2, there is shown a preferred embodiment of a device for making measurements with respect to the body of the patient. The device, which is generally denoted 10, includes a frame construction 12 comprising side frame members 12a and 12b and upper and lower frame members 12c and 12d. Frame 12 supports a non-opaque sheet-form viewing screen 14. Preferably, screen 14 is substantially transparent so that at least the silhouette of a patient standing behind the screen can be seen through the screen. The surface of screen 14 is marked off with equally spaced horizontal and vertical lines 14a and 14b forming a measuring grid. In addition, screen 14 includes measurement graduations 14c which are located centrally of screen 14 and extend vertically from between the top and bottom.

A horizontal measuring bar 16 is mounted on side frame members 12a and 12b to permit up and down movement of the bar. Bar 16 includes vertically extending slide members 16a and 16b at opposite ends thereof. Slide member 16a, 16b each include a pair of vertically spaced gear members 18 which engage and ride on respective toothed tracks 20 located on side frame members 12a and 12b so as to provide vertical movement of bar 16. Bar 16 also includes measurement graduations 16c along the length thereof, as illustrated.

Figure 4:
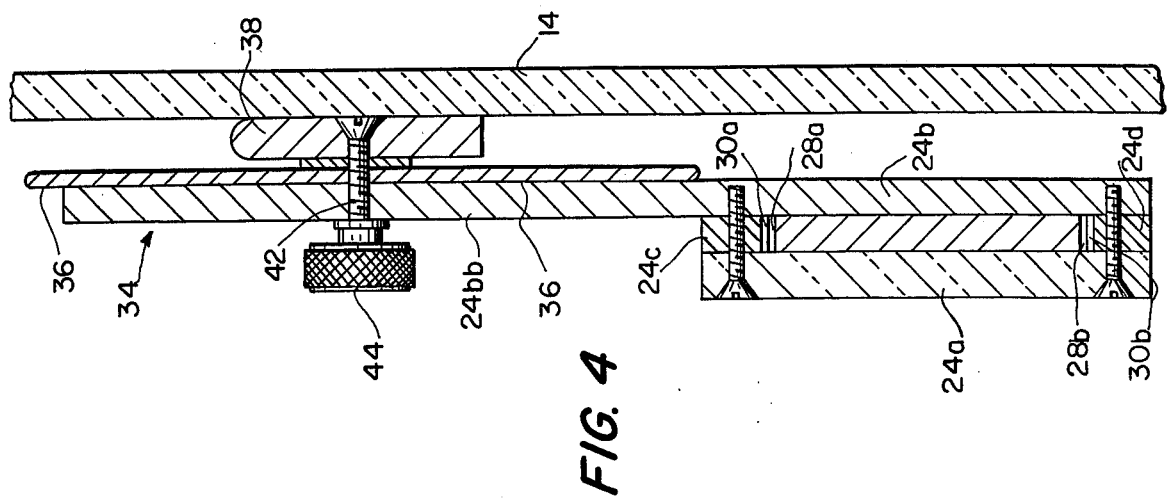
FIG. 4 is a sectional view taken generally along line IV—IV of FIG. 3.
Figure 3:
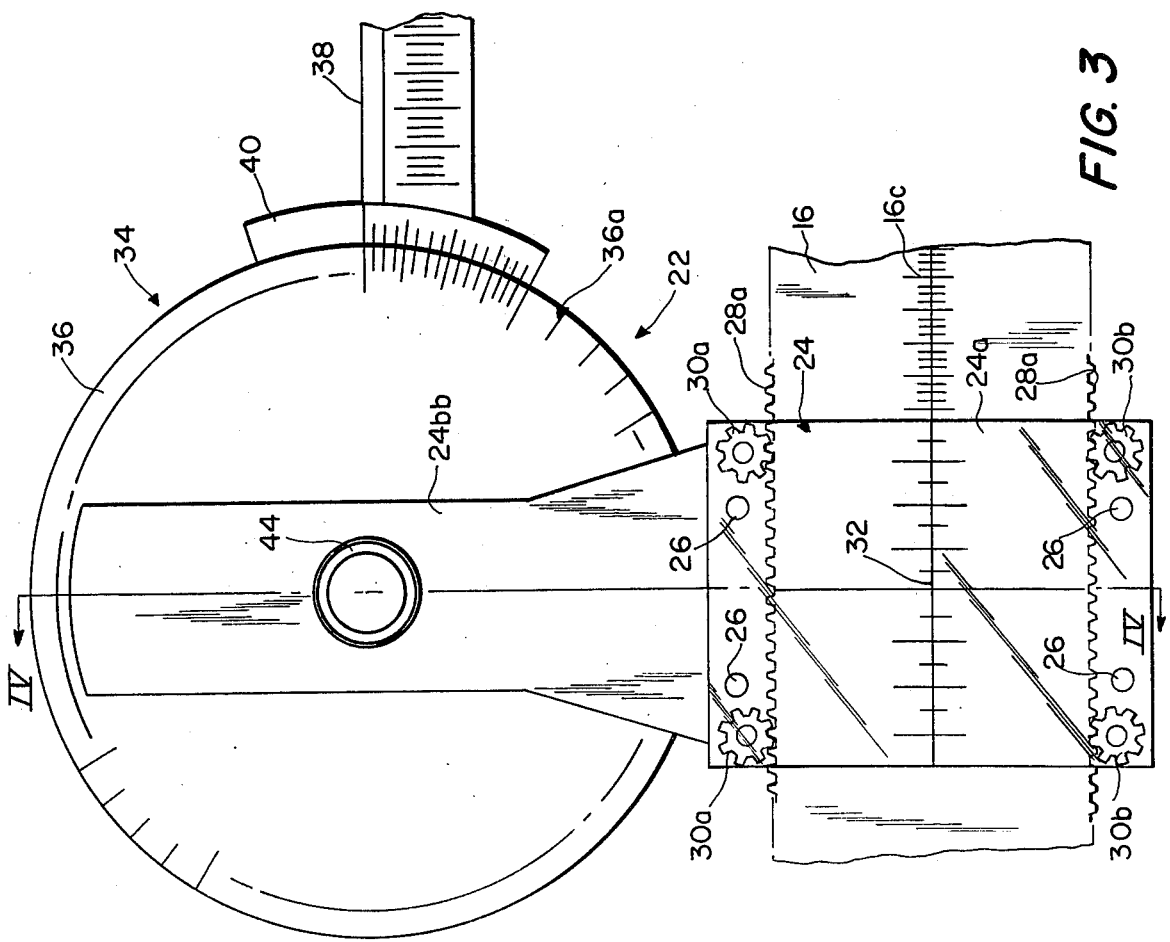
FIG. 3 is detail, in front elevation, of the angle measuring device shown in FIGS. 1 and 2.

An angle measuring device 22 is mounted for sliding movement along bar 16. The angle measuring device 22, which is shown in more detail in FIGS. 3 and 4, includes a base support and slide member 24. Support and slide member 24 comprises an outer face plate 24a and an inner support plate 24b which is joined to face plate 24a by screws 26 and is spaced from plate 24a by upper and lower spacer strips 24c and 24d so as to form a slot 28 therebetween (see FIG. 4.) Bar 16 is received in slot 28 and includes first and second tracks 28a and 28b located on, and extending along, the upper and lower edges thereof, respectively. Face plate 24 is fabricated of a transparent plastic or the like and cooperates with support plate 24 to carry upper and lower pairs of gear members 30a and 30b which are mounted between face plate 24a and support plate 24b, and engage and ride on toothed tracks 28a and 28b, respectively. Face plate 24a also includes cross hairs 32 which enable the angle measuring device 22 to be lined up with the graduations 16c on bar 16.

Support plate 24b includes a support tongue 24bb which serves to mount a protractor assembly 34. Protractor assembly 34 includes a circular plate 36 which is graduated in degrees aroung the peripheral edge thereof, as indicated at 36a, and a rotatable measuring arm 38 and an associated arcuate-shaped vernier 40, which are affixed to a central screw shaft 42 rotatably mounted in support tongue 24bb. The angle measuring arm 38 is rotatable about the axis of shaft 42 relative to circular plate 34 and cooperates with the latter to provide angular measurements. A knurled control knob 44, disposed at the end of shaft 40, can be used in controlling the angular movement of angle measuring arm 38.

Referring again to FIGS. 1 and 2, frame 12 is spaced from the wall by outwardly extending strut members 50 so that a patient, indicated at P in FIG. 2, can stand behind screen 14. A platform 52 is also provided behind screen 14 and the upper surface of platform 52 is aligned with the zero mark of the vertical measurement graduations 14c so that the patient is properly oriented with respect to the measurement coordinates provided.

In accordance with a further feature of the invention, an x-ray light box or frame 60 is provided which can be pivoted into position behind screen 14, FIG. 1 illustrating x-ray light box 60 in the operative position thereof behind screen 14 and FIG. 2 illustrating x-ray light box 60 in the inoperative position thereof. A support arm 62 is secured to the back of box 60 and is connected at the end thereof to a pivot assembly 64. The latter forms a pivot axis which permits light x-ray box 60 to be swung or pivoted to the operative position behind screen 14 (see FIG. 1) from an inoperative or rest position wherein box 60 lies in a plane generally perpendicular to the plane of screen 14 as illustrated in FIG. 2. With x-ray light box 60 in the latter position and an x-ray affixed to screen 14, the measuring apparatus described above can be used to make measurements relative to the x-ray. The pivot assembly 64, and thus box 60 and associated support arm 62, are mounted on a slide 66 which is, in turn, mounted for up and down movement along a track 68 extending parallel to frame member 12a. Thus, the vertical position of x-ray light box can be adjusted as desired.

X-rays to be examined can be secured to screen 14 in a number of ways, although, in accordance with a preferred embodiment, a number of relatively small checker-like magnetic discs are used in pairs to provide rapid, non-destructive mounting of the x-rays. It will be appreciated that the discs making up each pair are disposed on opposite sides of the screen 14 and are poled magnetically so to attract one another and thus hold the x-ray against screen 14. This is illustrated schematically in FIG. 2 by discs 70, 70 and x-ray sheet 72.

The operation of the measuring device of the invention will be evident from the foregoing description. In an exemplary case, the patient P stands behind screen 14 and the positions of measuring bar 16 and angle measuring device 22 are adjusted so as to properly line up with the portion of the body whose length, width or angle of slope is to be determined. Where, for example, one desires to ascertain the angle of droop or slope of a shoulder resulting from injury, the position of angle measuring device 22 is moved so that the angle measuring arm 38 is aligned with the shoulder and the angle of slope is directly read off of scale 36a. It will be appreciated that the device of the invention is extremely versatile and provides rapid, direct measurements which cannot be made with most conventional devices used for this particular purpose.

Although the invention has been described relative to an examplary embodiment thereof, it will be understood that other variations and modifications can be effected in this embodiment without departing from the scope and spirit of the invention.

I claim:

1. A device for making measurements with respect to the body of a patient or the like, said device comprising: a frame construction behind which the patient stands whose body measurements are to be determined, said frame construction comprising a frame and a non-opaque sheet-form viewing screen mounted by said frame and providing viewing of at least the silhouette of a patient standing behind said screen, said screen including a grid of horizontal and vertical measuring lines thereon;

a vertically extending measuring means centrally disposed on said viewing screen and graduated along the length thereof in measuring units;

a horizontally extending, vertically movable measuring bar graduated in measuring units along the length thereof;

means for mounting said measuring bar on said frame for relative movement with respect to said vertically extending measuring means; and an angle measuring means mounted on said measuring bar for movement along the length thereof, said angle measuring means including a pivotably mounted measuring member and means for indicating the angular position of said pivotably mounted measuring member, said pivotably mounted measuring member being graduated in measuring units along the length thereof, said angle measuring means comprising a slide member mounted for longitudinal movement along said measuring bar, and a part circular support plate graduated in degrees and carried by said slide member, said pivotably mounted measuring member being movable relative to said support plate to provide angular measurements, said measuring bar including at least one toothed track extending along the length thereof and said slide member of said angle measuring means includes at least one gear member which engages and rides on said toothed track, said device further comprising an x-ray light box, and pivotable mounting means connected to said frame for pivotably mounting said x-ray light box to permit movement of said light box between an operative position away from said screen and an operative position behind said screen for viewing through said screen.

2. A device as claimed in claim 1 wherein said measuring arm includes an arcuate shaped vernier movable therewith with respect to said support plate.

3. A device as claimed in claim 1 wherein said slide member includes a transparent face plate and a support plate spaced from said face plate so as to define a groove in which said measuring bar is received.

4. A device as claimed in claim 1 wherein said frame includes first and second side frame members each carrying track means, and said measuring bar includes slide members at the opposite ends thereof carrying gear means which engage said track means.

5. A device for making measurements with respect to the body of a patient or the like, said device comprising:

a frame construction behind which the patient stands whose body measurements are to be determined, said frame construction comprising a frame and a non-opaque sheet-form viewing screen mounted by said frame and providing viewing of at least the silhouette of a patient standing behind said screen;

a vertically extending measuring means centrally disposed on said viewing screen and graduated along the length thereof in measuring units;

a horizontally extending, vertically movable measuring bar graduated in measuring units along the length thereof;

means for mounting said measuring bar on said frame for relative movement with respect to said vertically extending measuring means; and an angle measuring means mounted on said measuring bar for movement along the length thereof, said angle measuring means including a pivotably mounted measuring member and means for indicating the angular position of said pivotably mounted measuring member, said pivotably mounted measuring member being graduated in measuring units along the length thereof, said device further comprising an x-ray light box, and pivotable mounting means connected to said frame for pivotably mounting said x-ray light box to permit movement of said light box between an operative position away from said screen and an operative position behind said screen for viewing through said screen.

6. A device as claimed in claim 5 wherein said pivotable mounting means further includes means for providing vertical movement of said x-ray light box relative to said screen.

7. A device as claimed in claim 5 further comprising magnetic means for releasably securing x-rays and the like to said screen.